United States Patent [19]
Crotty et al.

[11] Patent Number: 6,106,857
[45] Date of Patent: Aug. 22, 2000

[54] FRAGRANCED COSMETIC PRODUCT FOR REMOVAL OF KERATOTIC PLUGS FROM SKIN PORES

[75] Inventors: Brian Andrew Crotty, Branford; Philip Edward Miner, Newtown; Anthony Johnson, Fairfield; Alexander Paul Znaiden, Trumbull; Craig Stephen Slavtcheff, Guilford, all of Conn.

[73] Assignee: Chesebrough-Pond's USA Co., division of Conopco, Inc., Greenwich, Conn.

[21] Appl. No.: 09/227,516

[22] Filed: Jan. 8, 1999

Related U.S. Application Data

[60] Provisional application No. 60/077,614, Mar. 10, 1998.
[51] Int. Cl.$^7$ .............................. A61F 13/02; A61K 7/48
[52] U.S. Cl. ............................................ 424/448; 514/844
[58] Field of Search .................................. 424/448, 443; 514/844

[56] References Cited

U.S. PATENT DOCUMENTS

| | | |
|---|---|---|
| 4,126,142 | 11/1978 | Saute . |
| 4,752,472 | 6/1988 | Kligman . |
| 4,762,124 | 8/1988 | Kerch et al. . |
| 4,990,339 | 2/1991 | Scholl et al. . |
| 5,026,552 | 6/1991 | Gueret et al. . |
| 5,254,338 | 10/1993 | Sakai et al. . |
| 5,466,456 | 11/1995 | Glover . |
| 5,512,277 | 4/1996 | Uemura et al. . |
| 5,605,694 | 2/1997 | Nadaud et al. . |
| 5,723,138 | 3/1998 | Bae et al. . |
| 5,736,128 | 4/1998 | Chaudhuri et al. . |
| 5,811,107 | 9/1998 | Gangadharan et al. . |
| 5,935,596 | 8/1999 | Crotty et al. . |

FOREIGN PATENT DOCUMENTS

| | | |
|---|---|---|
| 206114 | 11/1959 | Austria . |
| 0 063 875 | 11/1982 | European Pat. Off. . |
| 0 514 760 | 11/1992 | European Pat. Off. . |
| 525530 | 2/1993 | European Pat. Off. . |
| 0 750 905 | 1/1997 | European Pat. Off. . |
| 2 734 574 | 11/1996 | France . |
| 44 33 191 | 3/1996 | Germany . |
| 9-194325 | 7/1997 | Japan . |
| 2 144 133 | 2/1985 | United Kingdom . |
| 87/05206 | 9/1987 | WIPO . |
| 93/05893 | 4/1993 | WIPO . |
| 96/08237 | 3/1996 | WIPO . |
| 96/14822 | 5/1996 | WIPO . |
| 97/32567 | 9/1997 | WIPO . |
| 98/05283 | 2/1998 | WIPO . |

OTHER PUBLICATIONS

Abstract of JP 63–57508(A), Mar. 12, 1988.
Abstract of JP 63–35511(A), Feb. 16, 1988.
Abstract of JP 55–127312(A), Oct. 2, 1980.
Patent Abstracts of Japan, 1983, JP 58021609A. (Kenji).
Patent Abstracts of Japan, 1983, JP 58021069A. (Yoichi).
Translation of KAO Biore Package (Japan)—1997.
"Proposing New Lifestyles. Superiior Product Creation: Biore Pore Back"—available from Internet: *URL:HTTP://WWW.KAO.CO.JP/AR97/PE.HTM*, 1997, XP002072734.

*Primary Examiner*—Thurman K. Page
*Assistant Examiner*—Alysia Berman
*Attorney, Agent, or Firm*—Milton L. Honig

[57] ABSTRACT

A cosmetic product is provided for removing keratotic skin plugs. The product is a strip sealed for storage having from 0.0001 to 2% fragrance within the atmosphere of the sealed pouch. The strip includes a flexible substrate sheet onto which a composition containing an adhesive polymer is deposited. Fragrance is immediately available upon opening the pouch. Since fragrance is invested on outer surfaces of the strip, a user can immediately smell the scent upon the application of the strip to the nose or other facial areas. There is no longer dependence for release of fragrance held within the adhesive polymer composition.

3 Claims, No Drawings

FRAGRANCED COSMETIC PRODUCT FOR REMOVAL OF KERATOTIC PLUGS FROM SKIN PORES

This application claims benefit of Provisional Appl. 60/077,614 filed Mar. 10, 1998.

BACKGROUND OF THE INVENTION

1. Field of the Invention

The invention concerns a fragranced cosmetic product effective for the removal of keratotic plugs from skin pores.

2. The Related Art

Highly visual pores on facial skin surfaces are perceived, especially by women, to be a serious beauty problem. The conspicuous nature of this problem is caused by keratotic plugs formed within pores of the skin. Keratotic plugs are dead epidermal cells keratinized together with sebaceous matter and dirt. Absent proper treatment, not only will beauty suffer but also various dermatological problems may arise. Removal with detergents or with make-up removers (e.g. cold cream) have not provided adequate solution to the problem. Squeezing the skin in an attempt to remove keratotic plugs can lead to infections which can damage skin.

Peelable masks have been employed to attack plugged facial pores. They are applied as mobile films to the skin and peeled off after drying. Typically, the film is a nonionic polymer such as polyvinyl alcohol or polyvinyl pyrrolidone. Unfortunately, the mask approach is still not sufficiently effective for removing dirt from skin pores and especially for removing keratotic plugs.

U.S. Pat. No. 5,512,277 (Uemura et al.) has reported a keratotic plug remover composition including use of a peelable mask formed from a resin functionalized with salt forming groups. Particularly preferred are cationic polymers which may be delivered as a poultice.

U.S. Pat. No. 4,126,142 (Saute) describes the use of sodium polystyrene sulfonate applied as a film to the face for cleansing skin and diminishing wrinkles.

Both Uemura et al. and Saute have examples which incorporate perfume or fragrance within the formulations. Neither appreciate that perfume will not readily release from a semi-solid or solid composition, especially when in contact on skin for only a short period of time.

Within the last year the market has seen introduction of a new product form to remove blackheads and unclog pores. Pond's® and Jergens Biore® have offered cleansing strips for adhesively removing contaminants from the nose and other facial areas. These products do not contain any fragrance. A problem in the context of adhesive strips is that fragrances can interfere with adhesion of those strips to the skin.

A still further issue is avoidance of delivering too heavy an amount of perfume. It must be appreciated that a keratotic plug remover in the form of a peelable strip is generally placed in close proximity to the nose. Too little fragrance and there is no smell. Too much and the smell can become unpleasant.

Accordingly, it is an object of the present invention to provide keratotic plug removing products, especially strips, which deliver an immediate pleasant scent sensation.

Another object of the present invention is to provide keratotic plug removing products, especially strips, which provide a relaxing level of fragrance in insufficient amount to swamp smell receptors in the nose.

Still another object of the present invention is to provide keratotic plug removing products, especially strips, which despite the presence of fragrance do not allow the fragrance to interfere with adhesive properties of the strips.

These and other objects will become more apparent from the summary and detailed description which follow.

SUMMARY OF THE INVENTION

A cosmetic product for removing keratotic plugs from skin pores is provided which includes:

(A) a strip comprising:
  (i) a flexible substrate sheet; and
  (ii) a composition containing a polymer selected from the group consisting of anionic, cationic, nonionic, amphoteric, zwitterionic and polymer mixtures thereof deposited onto the substrate sheet, the composition increasing in tackiness upon being wetted just prior to use thereby enhancing the composition adhesivity to skin; and (B) a pouch sealably enclosing the strip, a fragrance also being enclosed but separate from the strip present in an amount from 0.00001 to 2% by weight of the strip.

DETAILED DESCRIPTION OF THE INVENTION

Now it has been discovered that immediate impact and highly controlled fragrance delivery can be accomplished in the context of strip products by investing fragrance within the product pouch. Investment is achieved in a variety of ways. Fragrance may be sprayed or deposited along an interior lining of the pouch. Alternatively fragrance may be trapped along the heat sealed edges of the pouch and released as a consumer tears through the heat seal to recover the strip. A still further approach is to spray or print fragrance on an upper or lower surface of the strip or any backing sheet onto which the strip may removably be supported. When the strip is sealed within a pouch, at least some of the topically deposited fragrance will volatilize into the pouch chamber.

Additional fragrance beyond the invested fragrance may also be present in the adhesive or resinous components of the strip. However, these are intended as adjunct only.

The term "fragrance" is defined as a mixture of odoriferous components, optionally mixed with a suitable solvent diluent or carrier, which is employed to impart a desired odor.

Perfume components and mixtures thereof may be obtained from natural products such as essential oils, absolutes, resinoids, resins and concretes, as well as synthetic products such as hydrocarbons, alcohols, aldehydes, ketones, ethers, carboxylic acids, esters, acetals, ketals, nitriles and the like, including saturated and unsaturated compounds, aliphatic, carbocyclic and heterocyclic compounds.

Suitable characteristics of such perfumes/fragrances can include at least one of the following, in any combination: (1) liquid or semi-liquid after mixing with the other components; (2) pleasant and/or clean odor when mixed with other components, e.g., one or more of lavender, violet, rose, jasmin, pine, woody, floral, fruity, lemon, lime, apple, peach, raspberry, strawberry, banana, plum, apricot, vanilla, pear, eucalyptus, aromatic, aldehydic, tutti frutti, oriental, sweet, amber, Paola, Muguet, Citron (lime) ella, and the like; (3) specific gravity (20/20) in the range of 0.600–1.300, preferably 0.800–1.100, each preferably varying 0.001–0.05, more preferably 0.008–0.020; (4) refractive index (20° C.) of 1.300–1.800, preferably 1.400–1.600, each preferably varying 0.001–0.05, more preferably 0.008–0.020; (5) saponification value of 5–300, preferably 10–250; and (6) having a flash point of 20–200 Pensky-Martens Closed Cup (P.M.C.C.) and 10–100 Tag-Closed Cup (T.C.C.).

Typical perfume ingredients which may be employed for the present invention can be selected from one or more of:

2-methoxy naphthalene
Allyl cyclohexane propionate
alpha-citronellal
alpha-ionone
alpha-Santalol
alpha-Terpineol
Ambrettolide
Amyl benzoate
Amyl cinnamate
Amyl cinnamic aldehyde
Aurantiol
Benzaldehyde
Benzophenone
Benzyl acetate
Benzyl salicylate
Beta-caryophyllene
beta-Methyl naphthyl ketone
Cadinene
Cavacrol
Cedrol
Cedryl acetate
Cedryl formate
Cinnamyl cinnamate
cis-Jasmone
Coumarin
Cyclamen aldehyde
Cyclohexyl salicylate
d-Limonene
delta-Nonalactone
delta-Undecalactone
Dihydro isojasmonate
Dihydro mycenol
Dimethyl acetal
Diphenyl methane
Diphenyl oxide
Dodecalactone
Ethyl methyl phenyl glycidate
Ethyl undecylenate
Ethylene brassylate
Eugenol
Exaltolide
Galaxolide
gamma-n-methyl ionone
gamma-Undecalactone
Geranial
Geranyl acetate
Geranyl anthranilate
Geranyl phenyl acetate
Hexadecanolide
Hexenyl salicylate
Hexyl cinnamic aldehyde
Hexyl salicylate
Hydroxycitronelial
Indole
Iso E super
Iso-Amyl salicylate
Iso-bornyl acetate
Iso-butyl quinoline
Iso-Eugenol
Laevo-Carvone
Lilial (p-t-bucinal)
Linalool
Linalyl acetate
Linalyl benzoate
Methyl cinnamate
Methyl dihydrojasmonate
Methyl-N-methyl anthranilate
Musk indanone
Musk ketone
Musk tibetine
Myristicin
Nerol
Oxahexadecanolide-10
Oxahexadecanolide-11
para-cymene
para-tert-Butyl cyclohexyl acetate
Patchouli alcohol
Phantolide
Phenyl ethyl alcohol
Phenyl ethyl benzoate
Phenyl heptanol
Phenylhexanol
Phexylethylphenylacetate
Thibetolide
Vanillin
Vertenex
Vetiveryl acetate
Yara-yara
Ylangene Suitable solvents, diluents or carriers for perfumes as mentioned above are for example: ethanol, isopropanol, diethylene glycol monoethyl ether, dipropyl glycol, triethyl citrate and the like.

Particularly preferred perfume components of the present invention are cyclic and acyclic terpenes and terpenoids. These materials are based upon isoprene repeating units. Examples include alpha and beta pinene, myrcene, geranyl alcohol and acetate, camphene, dl-limonene, alpha and beta phellandrene, tricyclene, terpinolene, allocimmane, geraniol, nerol, linanool, dihydrolinanool, citral, ionone, methyl ionone, citronellol, citronellal, alpha terpineol, beta terpineol, alpha fenchol, borneol, isoborneol, camphor, terpinen-1-ol, terpin-4-ol, dihydroterpineol, methyl chavicol, anethole, 1,4 and 1,8 cineole, geranyl nitrile, isobornyl acetate, linalyl acetate, caryophyllene, alpha cedrene, guaiol, patchouli alcohol, alpha and beta santalol and mixtures thereof.

Amounts of the fragrance may range from 0.00001 to 2%, preferably from 0.0001 to 1%, optimally from 0.01 to 0.5%, most preferably from 0.05 to 0.25% by weight of the strip.

Cosmetic products of the present invention are based on a strip including a flexible substrate sheet and an adhesive composition, the strip being held within a sealably enclosing pouch. The flexible substrate sheet is impregnated by an adhesive composition containing an anionic, cationic, nonionic, amphoteric or zwitterionic polymer. Mixtures may be of polymers within any one category or between different category types. Illustrative of the latter, and a preferred embodiment, is a combination of an anionic and nonionic polymer. In a dry state, the composition preferably but not necessarily is non-tacky to the touch. The impregnated substrate sheet is sealably enclosed in a pouch, particularly a laminated foil package to control moisture level.

Pouches of the present invention are normally of the laminated foil variety. These are heat sealed and utilize foils with very low vapor (e.g. moisture) transmission rates (a rate of transmission less than 5% per day, preferably less than 1% per day volatile fluid gain or loss). Walls suitable for the pouch may utilize polyester, polyethylene or polypropylene sheets, several layers of which can be laminated together. These layers may also be provided with a coating of wax or other volatile fluid impermeable material.

The product is used by removing the strip from its usually individually wrapped pouch and either directly wetting the composition on the sheet or indirectly by wetting the face in areas to be contacted by the composition. In either instance, the wetting agent interacts with the composition so it becomes tacky and sufficiently mobile to flow into skin pores. The time between removal of strip from the pouch and use may be anywhere from 5 seconds to several hours, usually from 10 to 20 seconds. Pure water is the preferred wetting agent. However, other liquid systems or gels could be employed. Suitable wetting agents would include alcohols such as ethanol, propanol, propylene glycol, polyethylene glycol, polypropylene glycol and especially mixtures of these alcohols with water. Gels would normally consist of structured liquids (particularly water) thickened with structuring agents such as Carbomer.

Subsequent to wetting, the composition is allowed to dry over the area of treatment. During drying the keratotic plugs stickingly adhere to the composition. Advantageously the drying period ranges from 1 minute to 5 hours, preferably from 5 minutes to 1 hour, optimally from 10 to 20 minutes. Thereafter, the dried composition with adhered plugs is peeled from the skin.

Mobility of the composition may be measured by yield point. The yield point should range from 1 to 400 Pascals, preferably from 20 to 200, optimally from 50 to 100 Pascals.

Nonionic polymers suitable for adhesive film deposition are the copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1.1) wherein such copolymers are 50% esterified with a saturated alcohol containing from 1 to 4 carbon atoms such as ethanol or butanol; and acrylic copolymers, terpolymers, etc., containing acrylic acid or methacrylic acid esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerized terpolymer of methacrylic acid, n-butyl acrylate and ethyl acrylate (e.g., in a weight percent ratio of 31:42:27, respectively).

Further examples of nonionic adhesive polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 under the trademark PVP K-90 and those having an average molecular weight of about 1,000,000 sold under the trademark of PVP K-120. Particularly preferred is poly(methyl vinyl ether/maleic anhydride) as an unneutralized resin available from ISP Corporation under the trademark Gantrez® S-97 BF.

Anionic adhesive polymers often are derived from the nonionic types which include carboxylic acid functions. Alkaline agents are employed to neutralize the carboxylic acid or anhydride transforming them into anionic salts. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanol-amine (MEA); diethanolamine (DEA); triethanolamine (TEA); monoisopropanolamine (MIPA); diisopropanol-amine (DIPA); triisopropanolamine (TIPA); and dimethyl stearamine (DMS). Most preferred is AMP.

Particularly preferred anionic polymers are the salts of poly(methyl vinyl ether/maleic anhydride) and polystyrene sulfonic acid. The former is obtained by at least partial neutralization of Gantrez® S-97 BF and the latter available from the National Starch & Chemical Company under the trademarks Versa TL-501 and Flexan® 130 having respective molecular weights of about 500,000 and 100,000. Other polymer films which may be employed and are commercially available as listed in the Table below.

TABLE I

| POLYMER TRADEMARKS (SUPPLIER) | CTFA DESIGNATIONS |
|---|---|
| Resyn ® 28-1310 (NSC) | Vinyl acetate/crotonic acid copolymer |
| Resyn ® 28-2930 (NSC) | Vinyl acetate/crotonic acid/vinyl neodecanoate copolymer |
| Resyn ® 28-2913 (NSC) | Vinyl acetate/crotonic acid/vinyl neodecanoate copolymer |
| Versatyl ® 40 (NSC) | Octylacrylamide/acrylates copolymer |
| Versatyl ® 42 (NSC) | Octylacrylamide/acrylates copolymer |
| Experimental Resin (NSC) | Vinyl acetate/vinyl neodecanoate/maleic half-ester |
| Ultrahold-8 ® (BASF) | Acrylate/acrylamide copolymer |
| Luviset ® CAP (BASF) | Vinyl acetate/crotonic acid/vinyl propionate copolymer |
| PVP K-30 (ISP) | PVP |
| PVP/VA E-335 (ISP) | PVP/Vinyl acetate copolymer |
| PVP/VA E-735 (ISP) | PVP/Vinyl acetate copolymer |
| Gantrez ® ES-225 (ISP) | Ethyl ester of PVM/MA copolymer |
| Gantrez ® ES-425 (ISP) | Butyl ester of PVM/MA copolymer |
| Gaffix ® VC-713 (ISP) | Vinyl caprolactam/PVP/dimethyl aminoethyl methacrylate copolymer |

Cationic adhesive polymers suitable for the present invention may be prepared as homo- or copolymers from monomers including:

Dimethyl aminoethyl acrylate (DMAEA), Dimethylaminoethyl methacrylate (DMAEMA), Dimethylaminopropylacrylamide (DMAPAAm), and Dimethylaminopropyl methacrylamide (DMAPMAAm) which are all (meth)acrylamides or (meth)acrylic acid esters having a dialkylamino group;

Dimethylaminostyrene (DMASt) and Dimethyaminomethylstyrene (DMAMSt) and the like which are styrenes having a dialkylamino group;

4-Vinyl pyridine and 2-vinyl pyridine which are vinyl pyridines; and

Quaternized products of these with a known quaternizing agent such as alkyl halide, benzyl halide, alkyl or aryl sulfonic acid, or dialkyl sulfate.

Among suitable amphoteric adhesive polymers are those derived from monomers such as:

N-(3-sulfopropyl)-N-acryloyloxyethyl-N,N-dimethylammonium betaine, N-(3-sulfopropyl)-N-methacroylamidepropyl-N,N-dimethylammonium betaine, N-(3-carboxymethyl)-N-methacroylamidepropyl-N,N-dimethylammonium betaine and N-carboxymethyl-N-methacroyloxyethyl-N,N-dimethylammonium betaine.

When the salt forming group of the cationic and amphoteric polymers is not ionized, it is preferred to ionize it via neutralization with known acids such as hydrochloric acid and sulfuric acid which are inorganic acids; acetic acid, propionic acid, lactic acid, succinic acid, glycol acid which are organic acids, or with known bases such as triethylamine, trimethylamine which are tertiary amines; ammonia; or sodium hydroxide.

Most polymers suitable for the present invention will be relatively brittle when dried. Therefore, they require a supporting surface which is a flexible substrate sheet. Substrate sheets of the present invention may either be occlusive or non-occlusive. Preferably but not necessarily the sheets are non-occlusive to allow water evaporation from the deposited polymer as the film maturates. Non-occlusivity or breathability is achieved either through use of a hydrophobic substrate having physical porosity (e.g. pore channels) or a hydrophilic substrate wherein the material of construction inherently allows for breathability. Suitable materials include cellulosics such as rayon, wool, cotton, linen, thermoplastic fibers and combinations thereof. They may be woven or nonwoven. Nonwoven rayon is a preferred substrate. Materials formed from combinations of cellulosic with thermoplastic fibers may also be employed. For instance, a hydrophilic polypropylene/rayon combination can be employed for the present invention.

It is advantageous to employ a ratio of composition to substrate sheet in amount ranging from 0.1:1 to 1,000:1, preferably 0.5:1 to 100:1 and optimally 0.8:1 to 10:1 by weight. The polymer ordinarily will constitute from 50 to 100%, preferably from 75 to 99%, optimally from 85 to 95% by weight of the composition deposited onto the substrate sheet.

Minor adjunct ingredients may also be included such as opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A non-woven resin bonded 100% rayon non-apertured fabric from Veratec® is employed as a flexible substrate. Poly(methyl vinyl ether maleic anhydride) commercially available as Gantrez S-97BF®, is coated by knife-over-roll (25 mil) on the flexible substrate. After coating, the combination of resin and substrate is dried to 75° C. in a convection oven. The resultant strip is a dry non-tacky to the touch article approximately 8 centimeters long and 2.5 centimeters wide.

Across the dried strip is sprayed a fragrance composition. The composition includes the following perfume components.

| PERFUME COMPONENT | WEIGHT % |
|---|---|
| Phenyl ethyl alcohol | 13.00 |
| Dihydromyrcenol | 5.00 |
| Linalool | 8.00 |
| Bergamot oil | 5.00 |
| Galaxolide IMP | 10.00 |
| Isolongifolanone | 5.00 |
| alpha-Methyl ionone Iso | 5.00 |
| Lyral (cycloaliphatic aldehyde) | 4.00 |
| Hexyl cinnamic aldehyde | 6.00 |
| Lynalyl acetate | 3.00 |
| Citronellyl acetate | 5.00 |
| Phenyl ethyl acetate | 6.00 |
| Acetyl tributyl citrate | 25.00 |

The amount of fragrance deposited on the strip is approximately from 0.1 to 1% by weight of the total strip.

Immediately after spraying, the strip is packaged in a laminated foil volatile substance impermeable pouch of approximate size 11 centimeters by 6.5 centimeters. Edges along the perimeter of the pouch are heat sealed to ensure fragrance remains within the pouch.

EXAMPLE 2

A non-woven polypropylene non-apertured fabric, Veratec® 2006094, is employed as a flexible substrate. Poly (dimethylaminopropylacrylamide) is coated by knife-over-roll (25 mil) on the flexible substrate. After coating, the combination of resin and substrate is dried to 75° C. in a convection oven. The resultant strip is a dry non-tacky to the touch article approximately 8 centimeters long and 2.5 centimeters wide.

| PERFUME COMPONENT | WEIGHT % |
|---|---|
| Benzyl salicylate | 6.00 |
| Coumarin | 4.00 |
| Phenyl ethyl alcohol | 10.00 |
| Lilial (acyl substituted aldehyde) | 5.00 |
| alpha-Methyl ionone Iso | 3.00 |
| Para-t-butyl cyclohexyl acetate | 6.00 |
| Dihydromyrcenol | 12.00 |
| Acetyl cedrene | 6.00 |
| Allyl amyl glycolate | 1.00 |
| Galaxolide IPM | 5.00 |
| Vanillin | 3.00 |
| Hexyl cinnamic aldehyde | 5.00 |
| Patchouli oil | 5.00 |
| Bergamot oil | 10.00 |
| Citronellol | 10.00 |
| Carbitol | 7.00 |

A polyester laminate sheet is unrolled along a conveyer belt. Above the transported strip are a series of nozzles which spray the fragrance mixture of perfume components listed above. Subsequent to the spray station, and before any significant evaporation occurs, the sheet is cut into rectangles 11.5 cm by 6.3 cm. Onto the fragrance sprayed surface is deposited the dried strip impregnated with poly (dimethylaminopropylacrylamide). Thereafter, a second of the fragranced sheets is applied in a registered manner over the dried adhesive strip and first sheet. Further along the assembly line heat/pressure is applied along the borders of the sheets to bond them together forming a pouch for the adhesive strip. Fragrance is thereby trapped within the pouch.

EXAMPLE 3

A non-woven resin bonded 100% rayon non-apertured fabric from Veratec® is employed as a flexible substrate. Polyvinylpyrrolidone/vinyl acetate copolymer, available from the ISP Corporation as E-335, is coated by knife-over-roll (25 mil) on the flexible substrate. After coating, the combination of resin and substrate is dried to 75° C. in a convection oven. The resultant strip is a dry non-tacky to the touch article approximately 8 centimeters long and 2.5 centimeters wide.

| PERFUME COMPONENT | WEIGHT % |
|---|---|
| Phenyl ethyl alcohol | 5.00 |
| Dihydromyrcenol | 8.00 |
| alpha-Methyl ionone Iso | 6.00 |
| Bergamot oil | 5.00 |
| Benzyl salicylate | 3.00 |
| Styrallyl acetate | 3.00 |
| Hedione | 5.00 |
| Lavindin oil abrialis | 10.00 |
| Lyral (cycloaliphatic aldehyde) | 1.00 |
| Patchouli oil | 8.00 |
| Lemon oil | 10.00 |
| Galoxolide DEP | 16.00 |
| Linalool | 5.00 |
| Acetyl cedrene | 5.00 |

A pouch is die-cut and formed in a manner similar to that described under Example 2. The only difference in the procedure is that the fragrance is applied only after the adhesive strip article has been placed on the first cut sheet. The perfume components listed in the above table are then applied as a fragrance composition along all four borders of the pouch forming sheet. Thereafter, the second sheet of equal diameter is registered over the adhesive strip and first sheet. Heat/pressure is then applied along borders of the sheets to form the pouch. Fragrance is entrapped along the borders. Upon opening the pouch, fragrance is released.

What is claimed is:

1. A cosmetic product for removing keratotic plugs from skin pores comprising:

(A) a strip comprising:
      (i) a flexible substrate sheet; and
      (ii) a composition containing a polymer selected from the group consisting of anionic, cationic, nonionic, amphoteric, zwitterionic and polymer mixtures thereof deposited onto the substrate sheet, the composition increasing in tackiness upon being wetted just prior to use thereby enhancing the composition adhesivity to skin;
      (iii) a fragrance deposited onto the composition, the fragrance being a mixture of odoriferous components; and
   (B) a pouch sealably enclosing the strip, an enclosed fragrance arising from volatilization of the deposited fragrance being enclosed but separate from the strip present in an amount from 0.00001 to 2% by weight of the strip.

2. The product according to claim 1 wherein the enclosed fragrance comprises a perfume component selected from the group consisting of terpenes, terpenoids and mixtures thereof.

3. The product according to claim 1 wherein the enclosed fragrance is present within the pouch at a level from 0.05 to 0.25% by weight of the strip.

* * * * *